United States Patent [19]
Arnett et al.

[11] Patent Number: 5,136,676
[45] Date of Patent: Aug. 4, 1992

[54] COUPLER FOR A LASER DELIVERY SYSTEM

[75] Inventors: Michael Arnett, Palo Alto; Dale Koop, Sunnyvale, both of Calif.

[73] Assignee: Coherent, Inc., Palo Alto, Calif.

[21] Appl. No.: 737,395

[22] Filed: Jul. 29, 1991

Related U.S. Application Data

[63] Continuation-in-part of Ser. No. 694,245, May 1, 1991, abandoned.

[51] Int. Cl.⁵ .......................... G02B 23/26; A61B 1/00
[52] U.S. Cl. ..................... 385/119; 385/117; 385/33; 385/118; 606/17; 606/18; 606/16; 606/19; 128/4; 128/6
[58] Field of Search ................ 385/33, 115, 116, 117, 385/118, 119; 606/7, 11, 15, 16, 17, 18, 19; 128/4, 6

[56] References Cited

U.S. PATENT DOCUMENTS

| | | | |
|---|---|---|---|
| 3,982,541 | 9/1976 | L'Esperance, Jr. | 128/6 |
| 4,091,814 | 5/1978 | Togo | 128/303.1 |
| 4,528,983 | 7/1985 | Erb | 128/303.1 |
| 4,611,888 | 9/1986 | Prenovitz et al. | 385/117 X |
| 4,761,054 | 8/1988 | Ishimori et al. | 385/100 |
| 4,917,083 | 4/1990 | Harrington et al. | 606/15 |
| 5,074,860 | 12/1991 | Gregory et al. | 385/117 X |

*Primary Examiner*—Brian Healy
*Attorney, Agent, or Firm*—Limbach & Limbach

[57] ABSTRACT

A coupler 30 for use with medical laser delivery systems is disclosed. The delivery system includes an articulated arm and an endoscope 42. The coupler 30 connects the arm to the endoscope. The coupler includes an axially extending tube 46 receivable in the bore 48 of the endoscope. The tube facilitates alignment of the coupler with the endoscope. The coupler is also provided with a telescope optical system (50, 52) for adjusting the diameter of the beam at the entrance to the endoscope to reduce clipping of the beam thereby enhancing transmission.

23 Claims, 5 Drawing Sheets

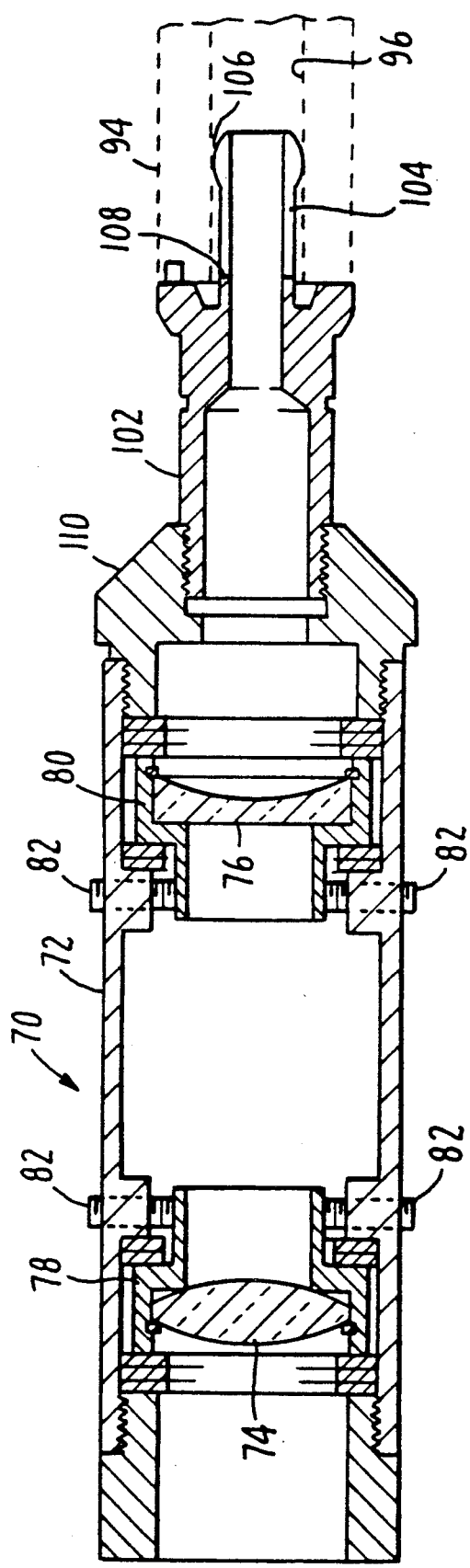
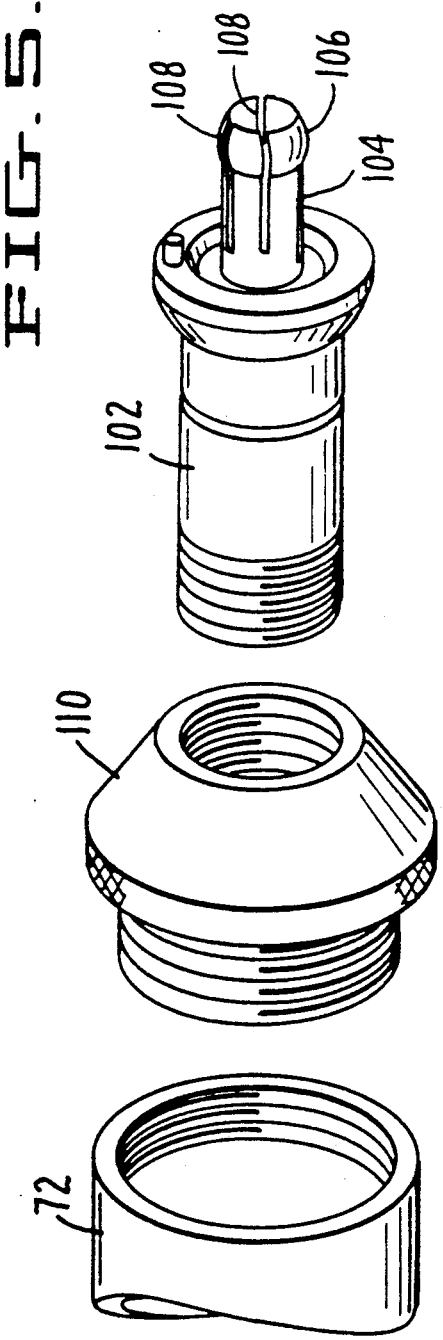
FIG. 5.
FIG. 6.

COUPLER FOR A LASER DELIVERY SYSTEM

This application is a continuation-in-part of previous copending application Serial No. 07/694,245, filed May 1, 1991, now abandoned.

TECHNICAL FIELD

A coupler is disclosed particularly suited for use in surgical laser beam delivery systems. The coupler is configured to improve the efficiency of the transmission of the laser beam through the delivery system.

BACKGROUND OF THE INVENTION

The use of lasers in various medical procedures is becoming quite common. The type of device used to deliver the laser energy from the laser to the treatment site is primarily dependant upon the wavelength of light generated. For example, 1.06 micron radiation generated by a Nd:YAG laser is typically delivered by an optical fiber formed from a silica compound. In contrast, 10.6 micron radiation generated by a $CO_2$ laser is typically delivered through an articulated arm assembly since presently existing optical fibers will not efficiently transmit such longer wavelength radiation.

The present invention is intended for use with an articulated arm. The arm consists of a number of hollow segments connected by rotatable joints. Mirrors are located in each of the joints to redirect the laser beam down the next segment of the arm. One end of the arm is connected to the output of the laser while the other end carries a delivery element.

The delivery element is selected based on the type of medical procedure which is to be performed. A common delivery element is an endoscope 10 which is illustrated in cross section in FIG. 1. The endoscope in FIG. 1 is of the type that might be used in a laparoscopy and is often referred to as a laparoscope.

As seen in FIG. 1, the laparoscope body will typically have a number of axially extending bores 12, 14, 16 and 18. The laser beam may be directed through bore 12. Bore 14 may be used for optical feedback so the surgeon can view the tissue site. The two smaller bores 16 and 18 can be used to deliver illumination via fiber optic bundles to the treatment site.

In the prior art, a coupler is used to join the end of the articulated arm to the entrance of the endoscope. In the present commercial environment, a number of medical device companies manufacture and sell endoscopes each of which have slightly different entrance end configurations. For each different endoscope design, there exists a coupler with a complimentary mating design.

While there exists a wide variety of prior art coupler designs, all of the existing designs have a few common features. For example, the coupler is typically provided with a conically shaped male mating end which is received in a conically shaped female mating configuration formed at the entrance of the endoscope. The mating conical configurations allow the two pieces to be adjusted when mounted. The alignment of the system relies heavily on the accuracy of the mating cones.

Unfortunately, the latter mounting approach has been less than satisfactory. More particularly, the prior approach required the doctor to adjust and test the alignment of the beam each time a new endoscope was attached. Since a new sterile endoscope is used for each new surgical procedure, the doctor must repeatedly adjust the alignment of the system. More significantly, even if the doctor is able to initially align the beam, the continuous movement of the articulated arm during the surgical procedure often results in the alignment being lost. If the alignment is lost, the percentage of the beam power transmitted down the endoscope is adversely affected. Moreover, misalignment of the components affects beam shape and size. Accordingly, it would be desirable to provide an improved coupler which could provide accurate and stable alignment of the mating components.

Another common feature of prior art couplers was the inclusion of a single, positive focusing lens. The lens was used to focus the beam entering the coupler from the articulated arm into the endoscope. The power of the lens was designed to bring the beam to a focus just beyond the distal end of the endoscope.

The latter design has been used quite successfully with endoscopes wherein the diameter of the bore was quite large. When the bore diameter is large, a high percentage of the beam can be injected down the endoscope. Recently, there has been a trend to develop endoscopes with smaller outer diameters and associated smaller axial bores. As can be appreciated, doctors prefer smaller diameter endoscopes because they are easier to handle and the associated incisions can be made smaller. There has also been a trend to develop endoscopes wherein the diameter of the bore used to transmit the laser beam is reduced while increasing the diameter of the bore of the viewing channel to improve visibility at the treatment site.

When the diameter of the axial bore for transmitting laser radiation is reduced for either of the above discussed reasons, problems have arisen with the coupling of the laser beam into the endoscope. FIG. 2 illustrates the problem. As can be seen, when the focal power of the lens 20 is selected to bring the focus of the beam 22 near the end 24 of the endoscope 26, the diameter $D_1$ of the beam at the entrance 28 will be significantly larger than the diameter $D_2$ of the endoscope bore. This disparity results in severe clipping of the beam at the entrance reducing the power injected into the endoscope.

A further complication arises as the articulated arm is moved during the procedure. As the arm moves, the level of clipping is varied and the delivered power continuously changes. In addition, the beam is distorted as it reflects off the bore. This distortion causes an irregular shape burn that constantly changes with arm movement. Accordingly, it would be desirable to provide an improved coupler which overcame these problems.

Accordingly, it is an object of the subject invention to provide a new and improved coupler for use with medical laser delivery systems.

It is another object of the subject invention to provide a coupler configured to improve the alignment with the endoscope.

It is a further object of the subject invention to provide a coupler having an axially projecting alignment tube, receivable within the bore of the endoscope for improving alignment.

It is still another object of the subject invention to provide a coupler having an improved focusing system.

It is still a further object of the subject invention to provide a coupler with a telescope focusing system for reducing the clipping of the beam entering the endoscope.

SUMMARY OF THE INVENTION

In accordance with these and many other objects the subject invention provides for a coupler for use in a medical laser system. The laser system is of the type that includes a laser for generating a beam of radiation. A delivery system is connected to the laser for delivering the beam to the treatment site. The delivery system includes an articulated arm and an endoscope. A coupler is provided for connecting the arm to the endoscope.

In accordance with the subject invention, the coupler is provided with an axially projecting tube which is receivable in the bore of the endoscope. The tube allows the position of the coupler to be registered with respect to the inner surface of the bore. By this arrangement, there is no need to independently adjust the alignment. In addition, the alignment will not drift due to the movement of the articulated arm during the surgical procedure.

In one embodiment, the tube extends substantially the length of the bore. In another embodiment, the tube is shorter and is provided with an adjustment feature to facilitate use with bores of slightly different diameters. In a further embodiment, an elastomeric ring is interposed between the coupler and the end of the endoscope so that registration is independent of the accuracy of the fabrication of the entrance configuration of the endoscope and relies entirely on the interaction between the tube and inner surface of the bore.

In another feature of the subject coupler, an improved focusing mechanism is provided. More specifically, a two element telescope is provided. The focal powers and positions of the elements are selected so that the diameter of the beam at the entrance of the endoscope is less than the diameter of the bore. In addition, the focal plane of the beam is located just beyond the distal end of the endoscope. By using this approach, the clipping problems of the prior art are avoided and more beam power will be transmitted down the endoscope.

Further objects and advantages will become apparent from the following detailed description taken in conjunction with the drawings in which:

BRIEF DESCRIPTION OF THE DRAWINGS

FIG. 3b is a schematic illustration of an alternate lens pair for use in the coupler shown in FIG. 3a.

FIG. 4b is a schematic illustration of an alternate is for use in the coupler shown in FIG. 4a.

FIG. 5 is a cross sectional view of a third embodiment of a coupler, formed in accordance with the subject invention shown in conjunction with an endoscope.

FIG. 6 is an exploded perspective view of the adapter flange of the coupler illustrated in FIG. 5.

DETAILED DESCRIPTION OF THE PREFERRED EMBODIMENTS

Figure 1:
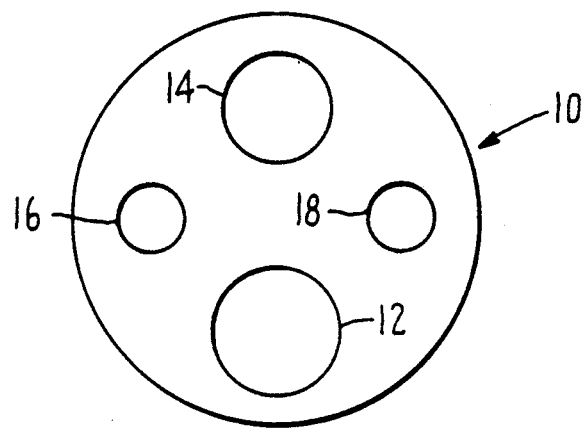
FIG. 1 is a cross sectional view of a conventional endoscope found in the prior art.
Figure 2:
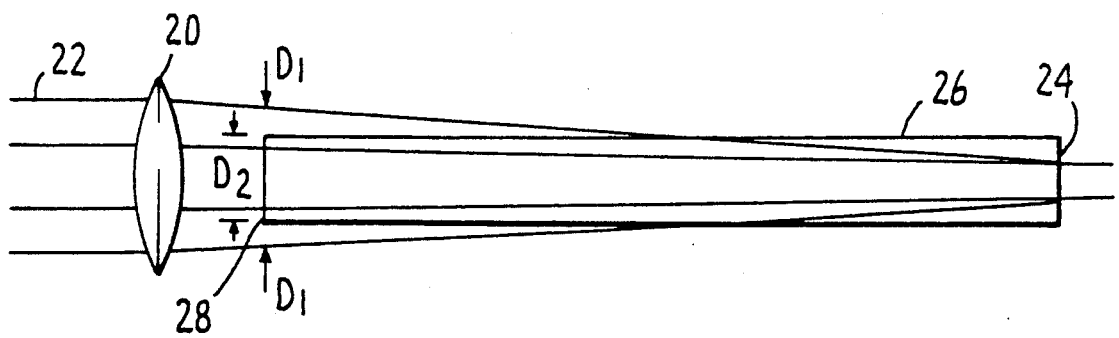
FIG. 2 is a schematic illustration of a coupler lens and an endoscope found in the prior art.
Figure 3A:
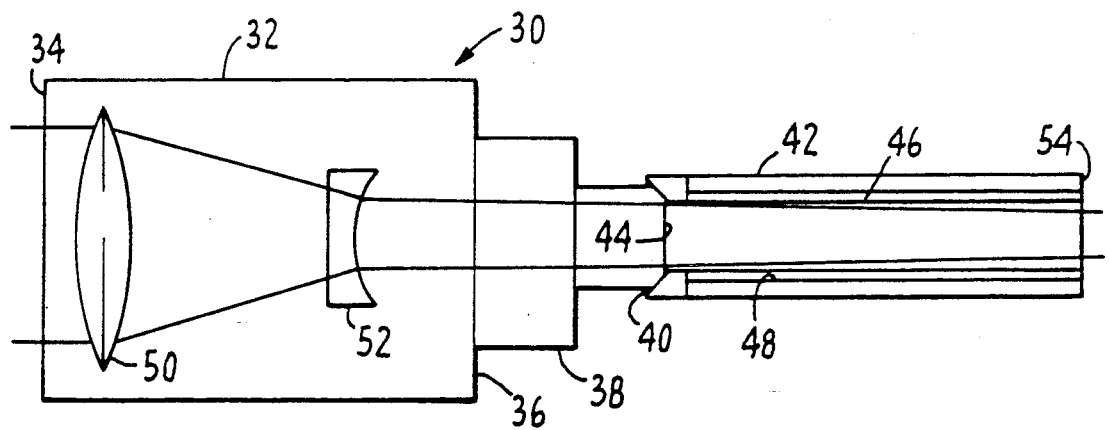
FIG. 3a is a schematic illustration of a coupler formed in accordance with the subject invention shown in conjunction with an endoscope.

Referring to FIG. 3a, there is illustrated a coupler 30 formed in accordance with the subject invention. Coupler 30 includes a body 32, one end 34 of which is connectable to an articulated arm (not shown). The opposed end 36 includes an adapter flange 38. Adapter flange 38 is configured to mate with the entrance end 40 of endoscope 42. As noted above, there are many manufacturers of endoscopes each using a different mating structure. The configuration of the distal end 44 of the flange 38 and the use of coupling nuts (if required) is dictated by the endoscope manufacturer and will be discussed in more detail below with respect to FIGS. 7 and 8.

In accordance with the subject invention, the distal end 44 of flange 38 is additionally provided with an axially projecting tube 46. Tube 46 is receivable in the bore 48 of the endoscope 40. In the embodiment illustrated in FIG. 3a, tube 46 extends substantially the length of the endoscope. The outer diameter of the tube is configured to be slightly less than the inner diameter of the endoscope. The minimum clearance should be about 0.001 inches so that the tube 46 can be easily slid into the bore.

As can be appreciated, the use of tube 46 results in the alignment of the coupler being registered exactly with the inner surface of the bore of the endoscope. By this arrangement, no adjustment is necessary when the endoscope is mounted to the coupler. In addition, the alignment will be maintained throughout the procedure.

FIG. 3a also illustrates the new focusing system of the subject coupler. The focusing system includes a first positive lens 50 for focusing the incoming laser beam. A second, negative lens 52 is provided downstream from the positive lens. The lens pair functions as a telescope to place the focus of the beam just beyond the distal end 54 of the endoscope. More significantly, the lens pair also adjusts the diameter of the beam at the entrance to the endoscope. In the preferred embodiment, the diameter of the beam at the endoscope entrance is less than the diameter of the bore so that clipping of the beam is avoided even where the diameter of the block is quite small.

The position of the lens pair can be fixed within the coupler. Alternatively, a means could be provided for adjusting the spacing between the lens pair so that spot size at the end of the endoscope could be varied.

Figure 3B:
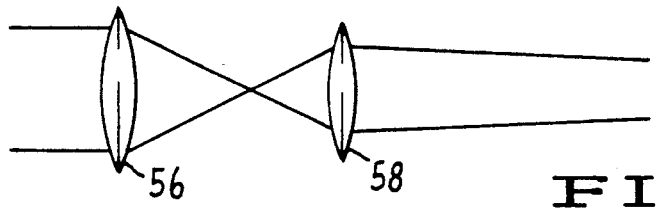

FIG. 3b illustrates an alternative lens pair that is optically equivalent to the pair shown in FIG. 3a. In FIG. 3b, both of the lenses 56 and 58 are positive elements.

Figure 4A:
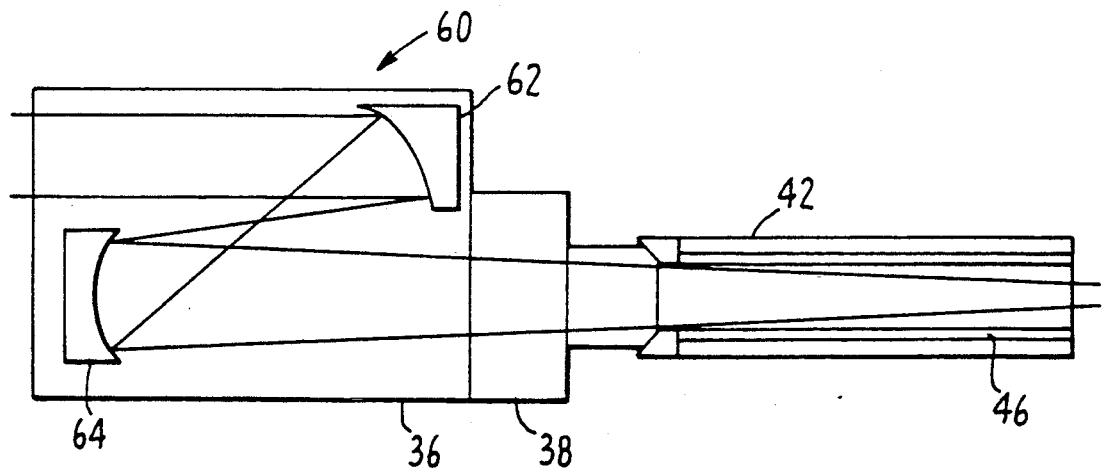
FIG. 4a is a schematic illustration of an alternate embodiment of a coupler formed in accordance with the subject invention shown in conjunction with an endoscope.
Figure 4B:
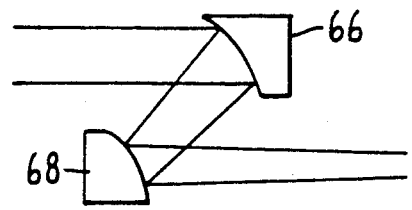

FIGS. 4a and 4b illustrate alternate embodiments of the subject coupler 60. In these embodiments, the focusing elements are defined by curved mirrors. In FIG. 4a, both of the mirrors 62 and 64 are positive elements. In FIG. 4b, the first mirror 66 is a positive element and the second mirror 68 is a negative element.

FIG. 5 is cross sectional view of a coupler 70 forced in accordance with the subject invention that has been fabricated and tested. The main body 72 of the coupler is configured to house and support the positive and negative lenses 74 and 76. Each lens is mounted in a lens cell 78 and 80. Each lens is mounted by inserting the associated lens cell into the body 72. Set screws 82 are used to lock the cells in place and permit some lateral alignment of the lenses.

Both of the lenses 74 and 76 are formed from zinc selenide which is transmissive to both visible and $CO_2$ radiation. The first lens 74 is provided with a focal length of 75 mm. The second lens is provided with a focal length of 50 mm and is spaced from the positive lens a distance of 30 mm. The negative lens is also spaced from the entrance end of the endoscope 94 by 50 mm. The endoscope 94 is 350 mm long.

The diameter of the incoming beam from the articulated arm is on the order of 8 mm. This diameter is reduced to about 4.8 mm in the plane of lens 76. The diameter of the beam at the entrance to the endoscope is on the order of 4.28 mm which is significantly less than the 5 mm of the bore 96.

It is desirable to allow some margin of error between the diameter of the aligned beam and the inner diameter of the bore since the position of the beam entering the coupler can vary depending on the extent of angular and positional errors (run-out) induced by the movement of the articulated arm. Good design of the articulated arm can minimize run-out errors. Existing arms manufactured by the assignee herein are specified to have a positional run-out limited to 2 mm and an angular run-out limited to 3 milliradians. It is anticipated that the beam entering the coupler should not exceed the limits of a 10 mm error circle. In this case, the subject lens system should allow nearly all of the beam to be injected into the bore of the endoscope.

The lens system will create a focal plane at the distal end of the endoscope approximately 350 mm away from the negative lens 76. The diameter of the beam at this location will be approximately 1.5 mm FIGS. 5 and 6 illustrate an alternative form for the flange 102 and alignment tube 104. As can be seen, tube 104 extends only a short distance, approximately 50 mm, down the length of the 350 mm bore of the endoscope. This configuration should be easier to fabricate and assemble. This configuration is also designed to be used with a variety of slightly different size bores.

To achieve this goal, the end of the tube 104 is provided with a radially projecting annulus 106. The diameter of the annulus 106 can be slightly larger than the inner diameter of the bore 96 of the endoscope. The annulus 106 is provided with a plurality of axially extending slots 108. Each slot 108 is about 0.200 inches long and 0.025 inches wide. The slots 108 allow for some compression of the tube into bores of slightly smaller diameter. This compression fit should enhance stability and help maintain alignment. A coupler nut 110 is provided to connect the flange 102 to the body 72.

Figure 7:
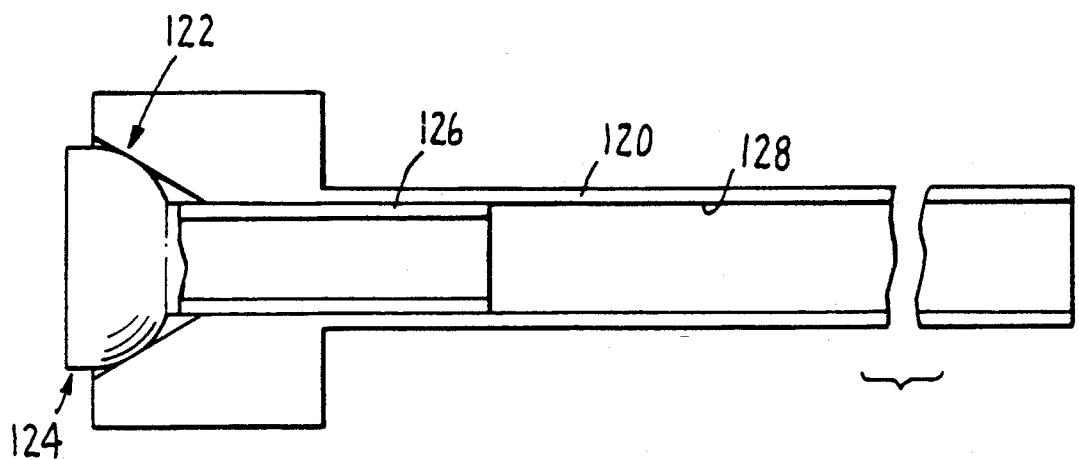
FIG. 7 is a schematic illustration of the mating end of the subject coupler for use with an endoscope having a conical female mating end.
Figure 8:
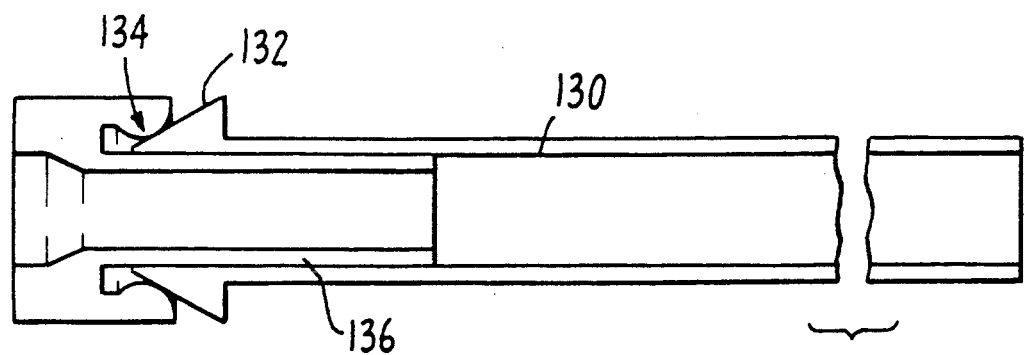
FIG. 8 is a schematic illustration of the mating end of the subject coupler for use with an endoscope having a conical male mating end.

FIG. 7 and 8 are two alternate configurations for the mating end of the subject coupler designed to interface with the mating ends of existing endoscopes. As noted above, in the prior art, the mating configurations were typically conical. The accuracy of these assemblies was dependent on the accuracy of the cones. These problems are overcome with the subject design.

FIG. 7 illustrates an endoscope 120 having a female mating cone 122. The mating end 124 of the flange of the subject coupler is provided with a spherical surface that centers itself in the female cone 122 independent of the accuracy of the angle of the female cone. Angular alignment of the coupler is then guaranteed by the axially extending tube 126 which projects into and registers with the bore 128 of the endoscope.

FIG. 8 illustrates an endoscope 130 having a male mating cone 132. The mating end 134 of the subject coupler is provided with a torroidal surface. As in the FIG. 7 embodiment, the torroidal surface centers on the male cone with alignment being provided by the axially extending tube 136.

As noted above there is a significant lack of accuracy in the manufacture of the prior art endoscopes. The approach shown in FIGS. 7 and 8 is intended to overcome variations in the angle of the conical surface provided at the entrance end of the endoscope. It has also been found that the axis of entrance configuration of an endoscope is often not collinear with the axis of the bore of the endoscope. Accordingly, if the flange of the coupler is rigidly connected and aligned with the axis of the entrance end of the endoscope, the accuracy of the alignment of the beam down the endoscope bore can be comprised.

Figure 9:
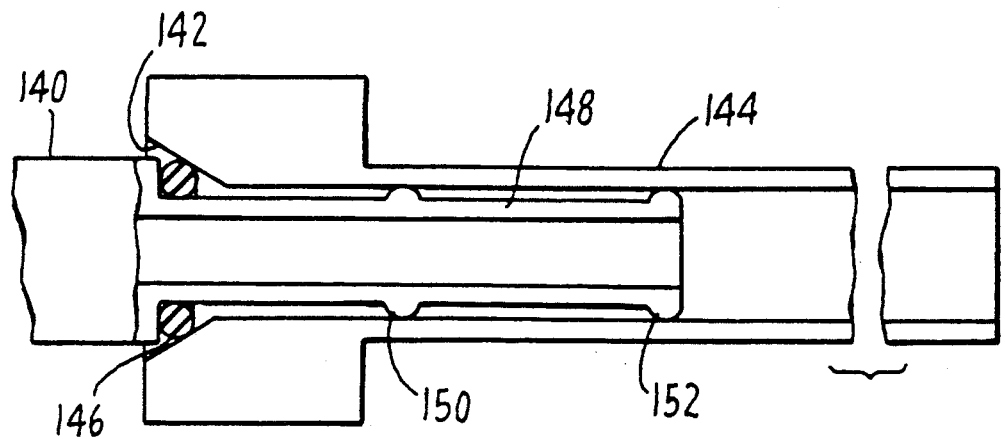
FIG. 9 is a schematic illustration of an alternate embodiment of the coupler of the subject invention shown with an endoscope having a conical female end.

The embodiment shown in FIG. 9 is designed to overcome the latter problem. In this embodiment, the flange 140 is not rigidly connected to the entrance 142 of the endoscope 144. In contrast, an elastomeric ring member 146 is inserted between the flange and the entrance 142. The ring 146 provides a seat and seal for the coupler while allowing the angle of the coupler to vary with respect to the endoscope bore. In this manner, the alignment of the coupler is not dependent on the accuracy of the construction of the entrance end configuration of the endoscope.

In this embodiment, the alignment of the coupler is based solely on the interface between the alignment tube 148 and the inner surface of the endoscope. In the embodiment shown in FIGS. 9 and 10, the alignment tube is provided with a pair of axially spaced annuli 150 and 152. These annuli are similar in function and structure to the annulus 106 illustrated in FIGS. 5 and 6. The second annulus 150 provides the extra kinematic support necessary in this configuration where the flange is floating with respect to the entrance of the endoscope. If annuli are not desired, it would be sufficient to extend the length of the alignment tube down a greater portion of the endoscope bore as shown in FIGS. 3 and 4.

Figure 10:
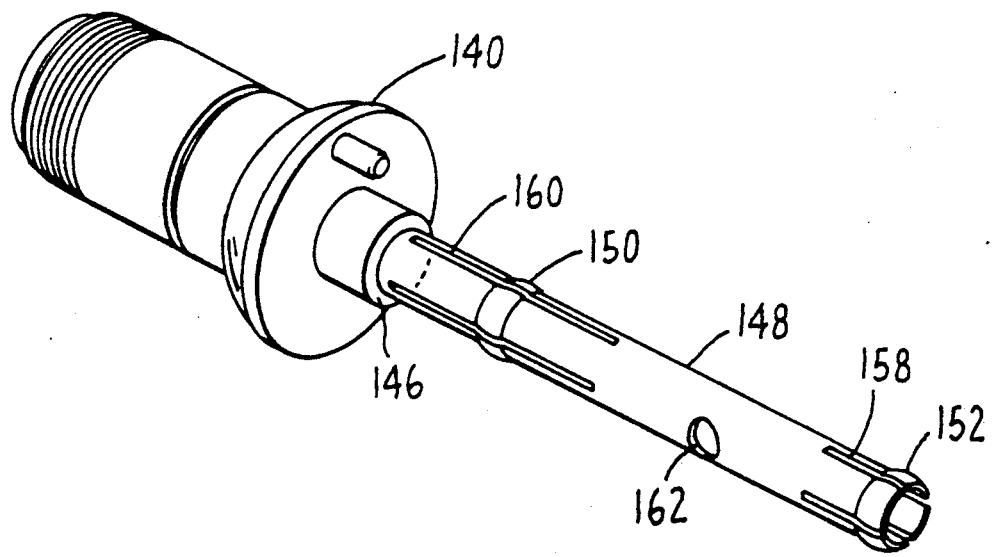
FIG. 10 is a perspective view of the coupler shown in FIG. 9.

FIG. 10 is a perspective view of a coupler which has been fabricated and tested. As in the embodiment of FIGS. 5 and 6, the annulus 152 is provided with a plurality of axially extending slots 158 running from the end of the tube 148 a distance of about 0.30 inches. A second set of slots 160 extend through the second annulus 150 and along the tube on either side of the annulus. The total length of slots 160 is on the order of 0.80 inches. The alignment tube 148 is 2.135 inches in length.

The elastomeric member 146 would be located at the end of the flange as shown in phantom line in FIG. 10. A suitable elastomeric member would be a rubber ring having a cross sectional diameter of 0.3 to 0.4 inches and formed from silicone rubber.

A purge gas is typically supplied to the treatment site through a fitting on the side of the endoscope (not shown). Hole 162 is provided in tube 148 to facilitate the flow of the purge gas.

The concept of using an elastomeric member as an interface between the flange and the endoscope can be extended to mating configurations other than the one shown in FIG. 9. For example, the ring could be used where the entrance end of the endoscope has a male conical configuration as shown in FIG. 8. A ring and flange structure could also be designed for use with the planar mating surface shown in FIG. 5.

In summary, there has been disclosed a new coupler for use with medical lasers. The coupler includes an axially extending tube receivable in the bore of an endoscope to improve alignment. In addition, a telescope optical system is disclosed for reducing the clipping of the beam at the entrance to the endoscope.

While the subject invention has been described with reference to the preferred embodiments, various charges and modifications could be made therein, by one skilled in the art, without varying from the scope and spirit of the subject invention as defined by the appended claims.

We claim:

1. A coupler for use with a medical laser system, said system including a laser for generating a laser beam and a delivery means, said delivery means including an arm connected to the output of the laser and an endoscope for insertion into the body of a patient, said endoscope having an axially extending bore through which the laser beam is transmitted, said coupler for joining the arm to the entrance of the endoscope, said coupler comprising:

a body, with one end of said body being connected to said arm and with the other end of said body including an adapter flange configured to mate with the entrance of the endoscope, said flange further including an axially projecting alignment tube receivable within the bore of the endoscope and being dimensioned to axially align the coupler with the endoscope.

2. A coupler as recited in claim 1 wherein said alignment tube includes a radially projecting annulus having an outer diameter substantially corresponding to the inner diameter of the bore of the endoscope.

3. A coupler as recited in claim 2 wherein said annulus includes an axial slot providing flexibility and allowing some variation in the outer diameter of the annulus.

4. A coupler as recited in claim 1 wherein said alignment tube extends substantially along the entire length of the endoscope.

5. A coupler as recited in claim 1 wherein the entrance end of the endoscope has a female conical configuration and wherein the mating surface of the flange is provided with a spherical configuration.

6. A coupler as recited in claim 1 wherein the entrance end of the endoscope has a male conical configuration and wherein the mating surface of the flange is provided with a torroidal configuration.

7. A coupler as recited in claim 1 further including an elastomeric member located between said flange and bearing upon the entrance to the endoscope to provide a seat for the flange without substantially limiting the alignment of the coupler.

8. A coupler as recited in claim 7 wherein said alignment tube includes a pair of axially spaced, radially projecting annuli each having an outer diameter substantially corresponding to the inner diameter of the bore of the endoscope.

9. A coupler as recited in claim 8 wherein each said annulus includes an axial slot providing flexibility and allowing some variation in the outer diameter of the annulus.

10. A coupler for use with a medical laser system, said system including a laser for generating a laser beam and a delivery means, said delivery means including an arm connected to the output of the laser and an endoscope for insertion into the body of a patient, said endoscope having an axially extending bore through which the laser beam is transmitted, said coupler for joining the arm to the entrance of the endoscope, said coupler comprising:

a body, with one end of said body being connected to said arm and with the other end of said body including an adapter flange, said flange further including an axially projecting alignment tube receivable within the bore of the endoscope through the entrance end thereof; and an elastomeric ring located between the flange and the entrance to the endoscope to provide a seat for the flange without substantially limiting the alignment of the coupler.

11. A coupler as recited in claim 10 wherein said alignment tube includes a pair of axially spaced, radially projecting annuli each having an outer diameter substantially corresponding to the inner diameter of the bore of the endoscope.

12. A coupler as recited in claim 11 wherein each said annulus includes an axial slot providing flexibility and allowing some variation in the outer diameter of the annulus.

13. A coupler for use with a medical laser system, said system including a laser for generating a laser beam and a delivery means, said delivery means including an arm connected to the output of the laser and an endoscope for insertion into the body of a patient, said endoscope having an axially extending bore through which the laser beam is transmitted, said coupler for joining the arm to the entrance of the endoscope, said coupler comprising:

a body, with one end of said body being connected to said arm and with the other end of said body including an adapter flange configured to mate with the entrance of the endoscope, said flange further including an axially projecting alignment tube receivable within the bore of the endoscope and being dimensioned to axially align the coupler with the endoscope;

a first focusing element located in said body; and a second focusing element located in said body between said second focusing element and said endoscope, with the focal powers of said focusing elements being selected such that the diameter of the laser beam at the entrance to the endoscope is less than the inner diameter of the bore of the endoscope and with the laser beam being brought to a focus proximate to the opposed end of the endoscope.

14. A coupler as recited in claim 13 wherein said focusing elements are mirrors.

15. A coupler as recited in claim 13 wherein said focusing elements are lenses.

16. A coupler as recited in claim 13 wherein said alignment tube includes a radially projecting annulus having an outer diameter substantially corresponding to the inner diameter of the bore of the endoscope.

17. A coupler as recited in claim 16 wherein said annulus includes an axial slot providing flexibility and allowing some variation in the outer diameter of the annulus.

18. A coupler as recited in claim 13 wherein said alignment tube extends substantially along the entire length of the endoscope.

19. A coupler as recited in claim 13 wherein the entrance end of the endoscope has a female conical configuration and wherein the mating surface of the flange is provided with a spherical configuration.

20. A coupler as recited in claim 13 wherein the entrance end of the endoscope has a male conical configuration and wherein the mating surface of the flange is provided with a torroidal configuration.

21. A coupler as recited in claim 13 further including an elastomeric member located between said flange and bearing upon the entrance to the endoscope to provide a seat for the flange without substantially limiting the alignment of the coupler.

22. A coupler as recited in claim 21 wherein said alignment tube includes a pair of axially spaced, radially projecting annuli each having an outer diameter substantially corresponding to the inner diameter of the bore of the endoscope.

23. A coupler as recited in claim 22 wherein each said annulus includes an axial slot providing flexibility and allowing some variation in the outer diameter of the annulus.

* * * * *